United States Patent
Hayward et al.

(10) Patent No.: US 9,592,195 B2
(45) Date of Patent: Mar. 14, 2017

(54) STABLE EFFERVESCENT BISPHOSPHONATE FORMULATIONS WITH RAPID SOLUBILIZATION CHARACTERISTICS

(75) Inventors: Marshall A. Hayward, Bridgewater, NJ (US); Timo Schmidt, Schindellegi (CH)

(73) Assignee: EffRx Pharmaceuticals SA (CH)

( * ) Notice: Subject to any disclaimer, the term of this patent is extended or adjusted under 35 U.S.C. 154(b) by 0 days.

(21) Appl. No.: 13/991,523

(22) PCT Filed: Dec. 5, 2011

(86) PCT No.: PCT/US2011/063341
§ 371 (c)(1),
(2), (4) Date: Jul. 11, 2013

(87) PCT Pub. No.: WO2012/078528
PCT Pub. Date: Jun. 14, 2012

(65) Prior Publication Data
US 2013/0287706 A1 Oct. 31, 2013

Related U.S. Application Data

(60) Provisional application No. 61/419,972, filed on Dec. 6, 2010.

(51) Int. Cl.
*A61K 9/46* (2006.01)
*A61K 31/683* (2006.01)
*A61K 31/663* (2006.01)

(52) U.S. Cl.
CPC .......... *A61K 9/0007* (2013.01); *A61K 31/663* (2013.01)

(58) Field of Classification Search
None
See application file for complete search history.

(56) References Cited

U.S. PATENT DOCUMENTS 4,687,662 A 8/1987 Schobel
5,415,870 A 5/1995 Gergely et al.
(Continued)

FOREIGN PATENT DOCUMENTS

| EP | 1197213 A2 | 4/2002 |
| GB | 2153225 | 8/1985 |
| WO | WO 2010/101537 | 9/2010 |

OTHER PUBLICATIONS

International Search Report for PCT/US0211/063341 dated Jun. 14, 2012.
(Continued)

*Primary Examiner* — Ernst V Arnold
*Assistant Examiner* — Kyung Sook Chang
(74) *Attorney, Agent, or Firm* — Neifeld IP Law

(57) ABSTRACT

A stable effervescent tablet, granule or powder composition free from excipients that may react with an effervescing organic acid component, comprising, an effective amount of a bisphosphonate bone resorption inhibitor, an effervescing organic acid component, an effervescing base component; wherein said composition is free of polyol binders and tableting lubricants; has a loss on drying of 0.25% (m/m) or less; has a complete disintegration time of no more than 180 seconds when placed in 3 to 8 fluid ounces of water at between 5-20° C.; and said bisphosphonate is incorporated as a micronized particle or by spray drying and is completely solubdised in water within 2 minutes without stirring.

15 Claims, 4 Drawing Sheets

(56) References Cited

U.S. PATENT DOCUMENTS

| | | |
|---|---|---|
| 5,462,932 A | 10/1995 | Brenner et al. |
| 7,488,496 B2 | 2/2009 | Rosen |
| 2001/0002395 A1 | 5/2001 | Daipotis et al. |
| 2001/0041165 A1 | 11/2001 | Katdare et al. |
| 2006/0240103 A1* | 10/2006 | McCallister et al. ......... 424/466 |

OTHER PUBLICATIONS

International Preliminary Report on Patentability for PCT/US0211/063341 dated Jun. 13, 2012.
Written Opinion of the ISA for PCT/US0211/063341 dated Jun. 13, 2012.
English translation of Abstract of CN 1934277 published Mar. 21, 2007.
European Search Report for Application No. 11846465.0.
International Search Report for PCT/US0211/063341 dated Jun. 14. 2012.

* cited by examiner

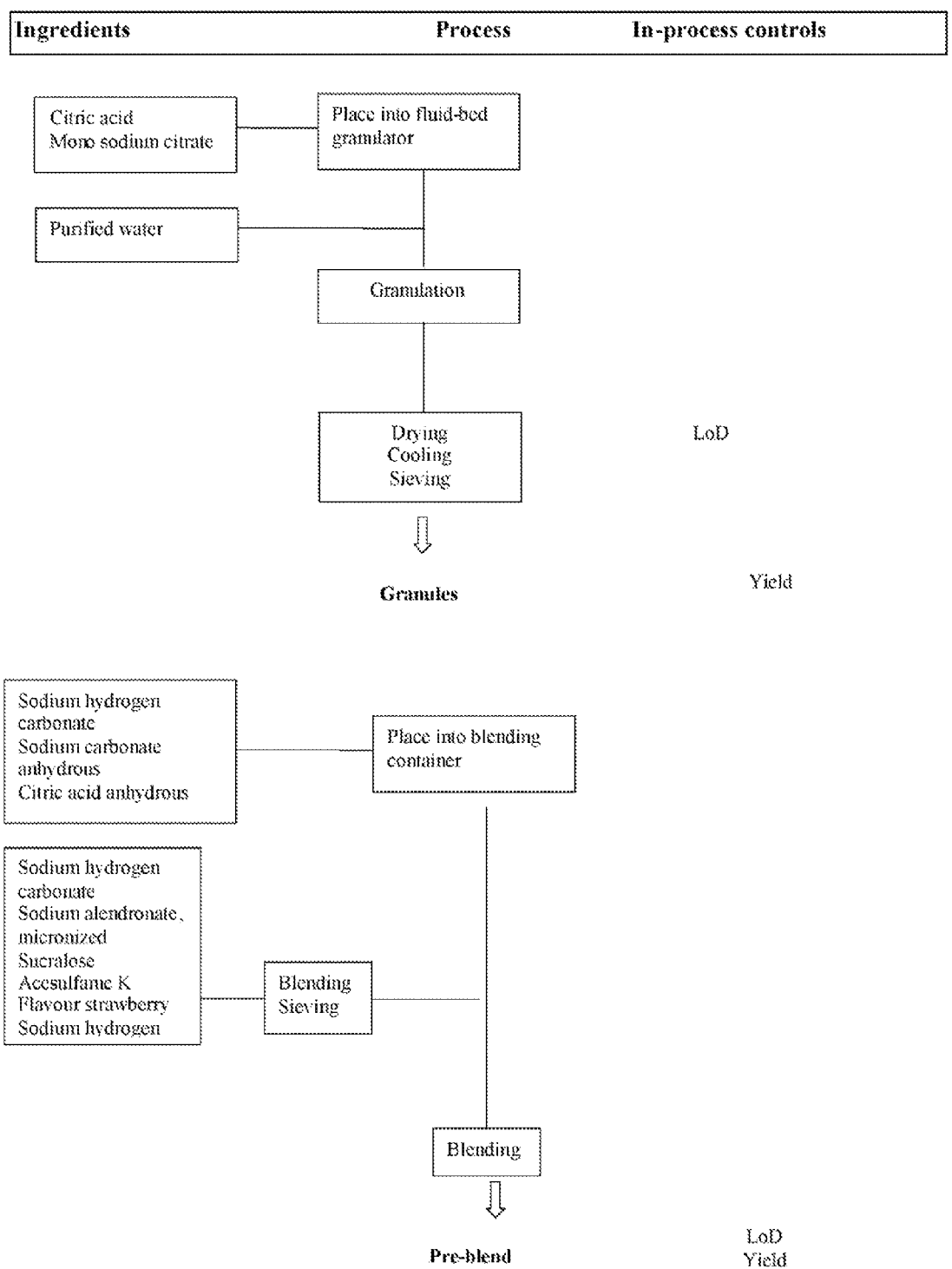
Figure 1A: Flow-chart of the manufacturing process

Figure 1B: Flow-chart of the manufacturing process
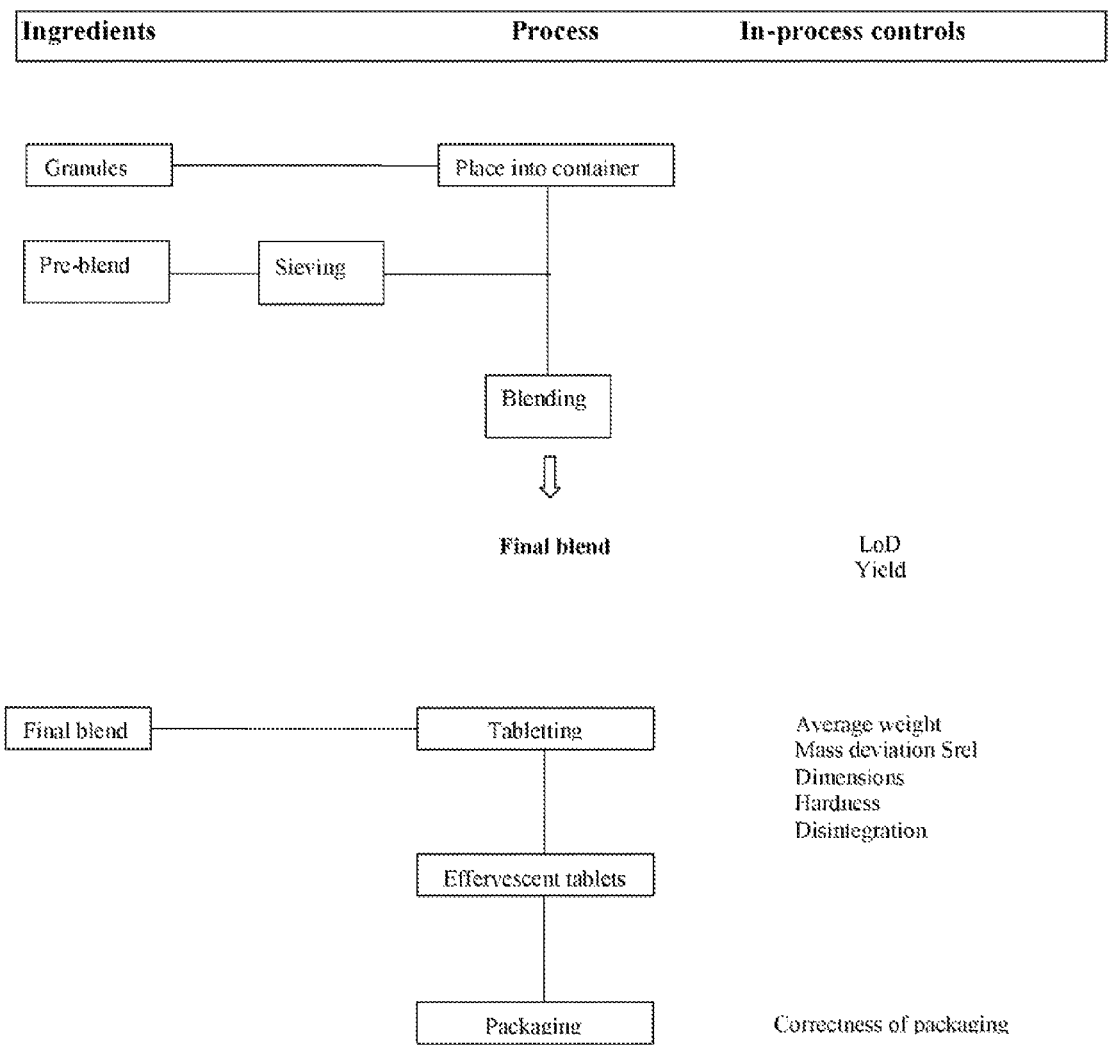

STABLE EFFERVESCENT BISPHOSPHONATE FORMULATIONS WITH RAPID SOLUBILIZATION CHARACTERISTICS

CROSS REFERENCE TO RELATED APPLICATIONS

This application is a national stage entry of PCT/US2011/063341, filed Jun. 14, 2012, which claims priority to U.S. Application No. 61/419,972, filed Dec. 6, 2010. The foregoing applications are incorporated by reference, herein, in their entirety.

FIELD OF THE INVENTION

The invention discloses storage-stable bisphosphonate formulations that are free of excipients which cause unwanted degradation products.

BACKGROUND OF THE INVENTION

Bisphosphonates are typically marketed in tablets, and the patient is instructed to take each tablet with a full glass of water in the morning, at least one-half hour before eating or drinking. However certain side effects, including esophageal irritation and mucosal erosion are frequently reported if a tablet is not taken with enough water, or if the patient does not remain in an upright position for at least one-half hour after taking the medication. in order to reduce such side effects it is known to prepare bisphosphonates in effervescent form, e.g Katdare et al., U.S. Pat. No. 5,853,759; U.S. patent application Ser. No. 10/092,083, filed Mar. 6, 2002 and U.S. patent application Ser. No. 10/273,081, filed Oct. 17, 2002, now U.S. Pat. No. 7,488,496; and U.S patent application Ser. No. 11/473,044, filed Jun. 23, 2006, all of which are incorporated herein by reference in their entireties.

In NDA 21-575, Merck and Company reported that of four test formulations of effervescent alendronate meant to be bioequivalent to Fosamax tablets, surprisingly, only two of the formulations had drug absorption comparable to the tablets. These data showed that effervescent and soluble formulations of bisphosphonates can be difficult to prepare as a suitable therapeutic delivery form. NDA 21-575 is a partially redacted document, so it is impossible to determine the full range and extent of components that were problematic.

Soluble effervescent formulations of bisphosphonate drugs have many potential advantages. When patients drink an effervescent liquid, it limits the amount of time in which the solid bisphosphonate is in contact with the esophageal tissue, minimizing the risk of irritation as compared to a tablet, which may lodge in the esophagus. Secondly the consistency of absorption of at least some of the bishosphonates, including alendronate, is enhanced. Thirdly, elderly patients who may experience difficulty in swallowing pills can more easily swallow a liquid formulation.

Regulatory requirements relating to effervescent bisphosphonate formulations required the use of ion chromatographic analytical methods to evaluate formulation stability, This analytical method revealed the formation of previously unknown and uncharacterized degradation products formed in conventional effervescent formulations upon storage.

In the course of conducting stability studies of alendronate formulations, unknown chromatographic peaks were identified after storage of tablets manufactured with conventional components such as polyols, sugar alcohols and other soluble materials known to the prior art for manufacture of effervescent tablets. These unknowns could only be visualized by the specialized and rarely utilized analytical technique of ion chromatography (I.C). I.C. is used to characterize bisphosphonate drug products because of a specific request by the United Kingdom Medicines and Health Regulatory Authority (MERA).

it appears that at elevated temperatures, acid components such as citric acid or citrate salts, in the presence of polyols (e.g. sugars such as sorbitol or materials such as polyethylene glycol or "PEG") give rise to unknown and unidentified materials. The detection system for I.C. uses very low wavelength ultraviolet light (the 'far ultraviolet' wavelength region) Most pharmaceutical products are assayed and detected by conventional chromatographic methods with analyte visualization at higher wavelengths (in the near ultraviolet) which do no detect these unknown peaks.

Investigation established that the degradation product did not come from the bisphosphonate, but involved widely used and standard functional excipients in the formulation. It is thought that these unknowns arise from esterification of sugars in the formulation. Sorbitol citrate reactions were described by Shogren, R. L., Doll, K. M. Gonzalez, S. O., Willett, J. L. Swift, G., *Preparation and Properties of Sorbitol Citrate Polyesters* Bioenvironmental Polymer Society Meeting. (p 93, Jun. 2006), in which sorbitol citrate polyesters We re prepared by melting mixtures of sorbitol and citric acid, mono- or di-sodium citrate at 110-200° C., then removing water of esterification in a vacuum oven, mixer or twin screw extruder. Esterification was confirmed by FTIR bands at 1735 and 1188 cm-1 and decreases in acid value of 20-80%. Reaction rates increased with increasing temperature, and sorbitol concentrations.

Reaction Chemistry

An acid catalyzed esterification and/or polymerization of acids and polyols (such as citrate and sorbitol or citrate and PEG) is believed to lead to the formation of unknown materials during storage. The instability, as judged by appearance of unknown peaks in I.C. chromatograms, is strongly correlated with elevated temperature of the product during storage. A binary combination of citrate and sorbitol generated the unknown peaks in large quantities. The recent publication by Shogren et al. cited above suggests that citric acid or citrate salts can combine with sugars to produce polyesters via a classic chemical reaction, a Fisher (acid catalyzed) esterification. One would expect that the combination of polyols and citrate, either in the solid phase or in solution could lead to the formation of esterification reaction products.

The problem was addressed by trying to eliminate the materials that give rise to the unknowns when combined with citrate (citrate being a necessary component of the effervescent system). Removal of sorbitol or other polyols from the formulation minimizes or eliminates the appearance of the unknown products, but the challenge then was to produce stable granules or tablets without using conventional pharmaceutical excipients.

SUMMARY OF THE INVENTION

One object of the invention is to provide a stable effervescent tablet, granule or powder composition free from excipients that may react with an effervescing organic acid component, comprising:

an effective amount of a bisphosphonate bone resorption inhibitor, an effervescing organic acid component, an effervescing base component;

wherein said composition is free of polyol binders and tableting lubricants; has a loss on drying of 0 25% (m/m) or less; has a complete disintegration time of no more than 180 seconds when placed in 3 to 8 fluid ounces of water at between 5-20° C., and said bisphosphonate is incorporated as a micronized particle or by spray drying and is completely solubilised in water within 2 minutes without stirring).

Another object of the invention is to provide a method of manufacturing a stable effervescent tablet granule or powder composition free from excipients that may react with a effervescing organic acid component, comprising:

blending in a fluid-bed granulator an effervescing organic acid component and an effervescing base component spray-granulated with purified water, and adding a daily, weekly, bi-weekly, or monthly oral dose of a bisphosphonate bone resorption inhibitor, wherein said composition is free of polyol binders and tableting lubricants, has a loss on drying of 0.25% (m/m) or less; has a complete disintegration time of no more than 180 seconds when placed in 3 to 8 fluid ounces of water at between 5-20° C. said bisphosphonate is incorporated as a micronized particle or by spray drying and is completely solubilised in water within 2 minutes without stirring, and, tableting the composition to achieve a tablet hardness of 35 to 120 Newtons.

BRIEF DESCRIPTION OF THE FIGURES

FIG. 1A is a flowchart showing the beginning of the manufacturing process.

FIG. 1B is a continuation flowchart showing the manufacturing process.

DETAILED DESCRIPTION OF THE INVENTION

Figure 2:
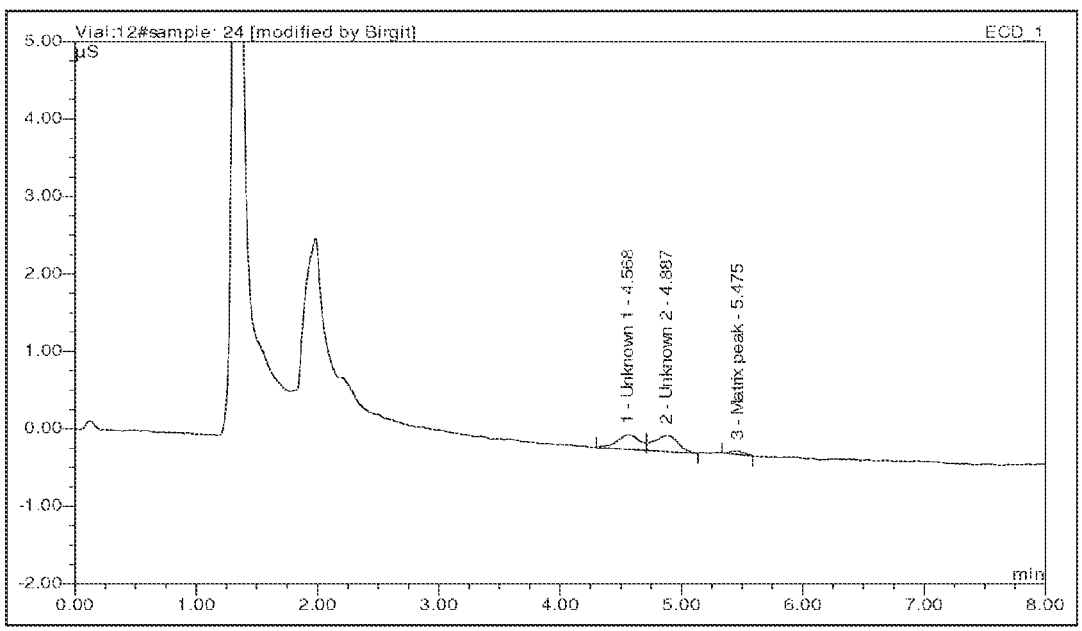
FIG. 2 is an ion chromatogram showing the impurity formed upon storage of the conventional effervescent alendronate formulation containing polyol in Example 1.
Figure 3:
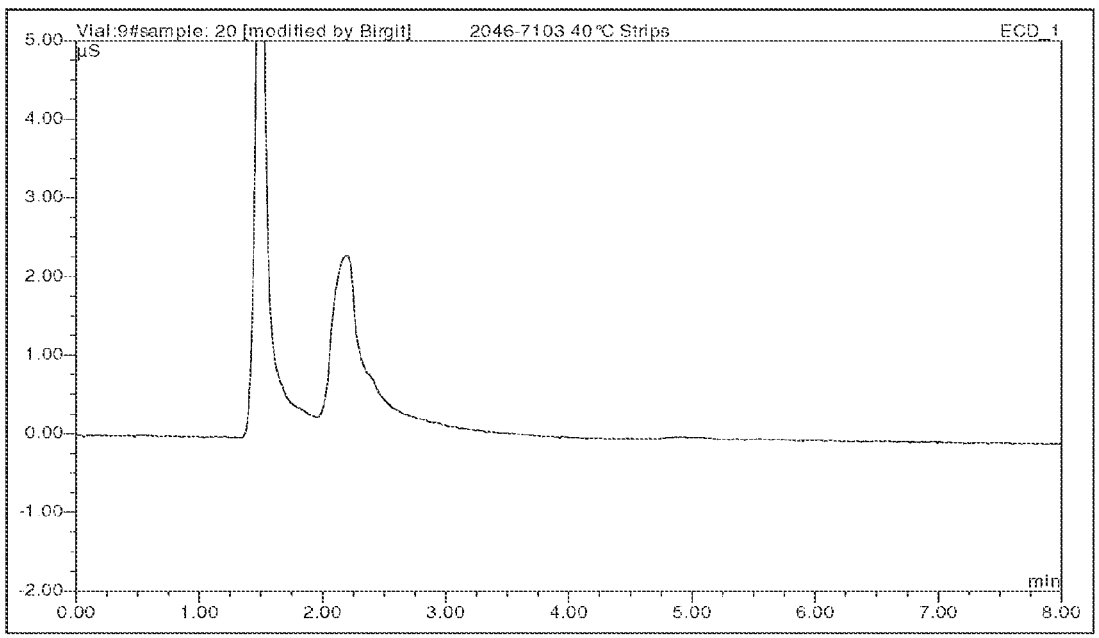
FIG. 3 is an ion chromatogram of a storage sample demonstrating that the impurity does not form in a formulation that excludes polyols.

A pilot scale reformulation was developed that has had an acceptable profile through 3 months on stability station. Clinical trial materials were prepared according to the same formula, and placed on storage. At 3 months accelerated stability, unknown peaks began to appear at the same retention time as with sorbitol/citrate; 6 months samples of the pilot batch also showed these degradation products. Further investigation has also shown that small quantities of unknown peaks are generated by (1) orange flavor+citrate and (2) PEG+citrate. No other components showed the unknown analytes. Since these observations have been made, it is clear that the flavors are manufactured with polyol carriers, and PEG of course is a polyol; hence., the appearance of the reaction products is consistent with the suspected reaction chemistry Temperature Dependence of Degradation Product Formation Pilot batches at 6 months show instability at 40° C., hints of instability at 30° C., but 25° C. samples show no stability concerns. Three month stability on a larger clinical trial supplies batch shows instability at 40°C., possible hints of instability at 30° C., and nothing untoward at 25° C. Longer term stability assays showed, as expected, that presence of the degradation products increases with time and thermal (elevated temperature) stress. The reaction is driven by elevated temperature releasing nascent water in the formula. Components yielding the Unknowns In addition to the recognized liabilities of sugars, alcohols, polyols other formula components can be problematic.

Flavors: Flavor oils per se are apparently not involved, but acids in combination with carriers in the flavor system (maltodextrin and other sugars present in very small quantities) can also cause the formation of the unknown analyte peaks.

Polyethylene glycol (PEG): PEG, a lubricant even if used in small quantities (25 mg/tablet), gives rise to unknown reaction products with citrate. PEG therefore needs to be eliminated in the formula, but not substituted with another excipient that normally leads to very poor tableting performance because of lacking lubrication.

Additional investigations were undertaken to assess the best flavors to incorporate in the effervescent formulation. That is, the flavors with the least potential to generate unknown reaction products. These were strawberry and apricot, which are stable in the product on storage.

Having identified a number of common functional components that are problematic in the formula, work was undertaken to develop a formula that was suitable as to material handling, content uniformity, and capable of being prepared as a tableted effervescent product.

Removal of all excipients which contributed to the observed degradation products solved the immediate problem of excipient degradation product formation, but the act of removing such key functional granulation and tableting excipients posed significant challenges with respect to tableting, disintegration, solubilization, and consumer acceptability. A in codified fotmulation and manufacturing process that maintains high consumer acceptability and tablet performance characteristics, while producing a stable and acceptable pharmaceutical product, was discovered.

Moreover, although the modified tablet formulation disintegrated rapidly with alendronate and other bisphosphonates, and most components fully dissolved in water, it was determined that alendronate itself did not solubulize rapidly. This behavior in effervescent formulations was surprising because alendronate itself is soluble in water.

Alendronate is used in the form of the sodium salt trihydrate in our formulations This drug has a recognized solubility of 10 mg/ml in water. Given the low molecular weight and polar nature of the drug, very rapid solubilization in water is expected.

However, a bioavailability/bioequivalence study testing the absorption of 70 mg effervescent alendronate, as compared to 70 mg Fosamax tablets, failed to demonstrate that soluble effervescent alendronate was bioequivalent to alendronate from Fosamax tablets. Investigation showed that this failure was because crystals of alendronate do not immediately dissolve in effervescent dosing solutions, and that the conventional particle size of alendronate API gives poor dissolution characteristics in effervescent media. Investigation showed that the alendronate which remained uninvested in the dosing glass led to under-dosing of the patient and lack of bioequivalence to Fosamax tablets.

After it was discovered that effervescent alendronate was not being fully ingested, even after complete tablet disintegration, crystals were visually observed at the bottom of the glass after Completion of tablet dissolution. Up until that time these remaining crystals were thought to be citric add or sodium citrate. To confirm their identity these crystals were isolated by filtration and chemically analyzed. Surprisingly, up to 20% of the nominal alendronate content of the effervescent tablets was recovered as insoluble alendronate Crystals in this manner. Experiments investigating the time to dissolution of these crystals in various formulas (with different alendronate particle size specifications) confirmed that alendronate particle size is a critical parameter with respect to dissolution, and aggressive mixing (solution swirling, stirring with a spoon, or even sonication) is required to fully dissolve alendronate over periods of 20 minutes or more after tablets are placed in water. Data summarizing the crystal solubility observations are in Table 1

Once the unexpected observation of peer alendronate solubilization was confirmed, different means to remedy the problem were evaluated. It became evident from dissolution trials with different particle size materials and from milling and sieving trials that particle size was indeed a critical parameter influencing dissolution and solubilization. Practical means to achieve desired product performance thus include, for example, using smaller and well-defined particle size distributions of alendronate, milling and sieving alendronate, and/or spraying alendronate onto other granular components of the drug product tableting blend.

Micronization and spray drying approaches were successful in achieving the necessary and desired rapid dissolution of alendronate from effervescent formulations. in the case of micronized and spray dried alendronate, it was observed that even without manual stirring or swirling, 100% solubilization of alendronate (as judged by visual examination as well as chemical analysis) was routinely achieved within 2 minutes of placing the tablet in water. Although the particle size of sprays alendronate is not known, it is reasonably assumed that the spray drying procedure results in particle sizes equivalent to the micronized alendronate powder conventionally blended into the tablets, as the dissolution time is similar and practically immediate. in the case of micronized alendronate, the particle size specification found to achieve suitable results is a mean particle size ($X_{50}$ or $50^{th}$ percentile) of about 6.2 microns (um), with $X_{10}$ (the 10th percentile) at about 2.7 microns and $X_{90}$ (the $90^{th}$ percentile) at about 13 microns.

In Table 1, comparative samples 1-4 are not suitable for commercialization or use as a therapeutic because the formulations do not perform satisfactorily with respect to dissolving time. Samples 5 and 6, however, are suitable.

TABLE 1

Relationship of Alendronate Particle Size in Tablets and Alendronate Dissolution in Water

| Alendronate particle size characteristics | Sample Number | $X_{10}$ (μm) | $X_{50}$ (μm) | $X_{90}$ (μm) | Time to complete crystal dissolution with stirring; visual with chemical assay confirmation |
|---|---|---|---|---|---|
| Alendronate (coarse particles) | 1 | 17.2 | 95.2 | 294.8 | 8.5 to 10.5 minutes |
| Alendronate (medium particles) | 2 | 40 | 109 | 198 | 4.5 to 5.5 minutes |
| Alendronate (medium-fine particle) | 3 | ND | 29.9 | 93.7 | 3.5 to 4 minutes |
| Alendronate (medium-fine particles as above that were milled and sieved to less than 63 microns) | 4 | ND | ND | Presumed less than 63 based on sieve fraction | 2.5 to 3 minutes |
| Alendronate (extremely fine, micronized) | 5 | 2.7 | 6.2 | 13 | Less than 2 minutes |
| Alendronate (extremely fine, dissolved in water and sprayed onto granules) | 6 | ND | ND | ND | Less than 2 minutes |

ND, unknown or Not Determined

For a soluble drug dosing form to be useful it is critical that the drug dissolve fully and rapidly in water with a minimum of patient involvement. For alendroante and other bisphosphonates, it is critical that an appropriately fine particle size of active drug be incorporated into the product formulation. Samples 5 and 6 satisfy this criteria, while samples 1-4 do not Phosphite/Phosphate are determined using ion chromatography with suppressed conductivity detection mode as limit test.

Detector: ED50 Electrochemical detector or equivalent
Column: precolumn in serie with 2 columns AS4a 250×4 mm from Dionex
Eluent:
A) 5 mM Sodium carbonat solution in water (gradient program) B) 20 mM Sodium carbonat solution in water
Suppressor: ASRS 4 mm, Current: about 50 mA
Flow: 2.0 ml/mm
Temperature: 20° C.
Solvent: distilled water (1 tablet/100 ml)

| t (min) | % A | % B |
|---|---|---|
| 0 | 100 | 0 |
| 7 | 100 | 0 |
| 8 | 0 | 100 |

-continued

| t (min) | % A | % B |
|---|---|---|
| 20 | 0 | 100 |
| 21 | 100 | 0 |
| 35 | 100 | 0 |

The change of composition between 7 and 8 min and 20 and 21 min is linear

EXAMPLE 1

| | Batch | |
|---|---|---|
| | 2046-4010, contains Polyols | 2046-7103, Polyol-free |
| Micronized Sodium alendronate EP | 91.37 mg | 91.37 mg |
| Monosodium citrate anhydrous DAC | 1820.00 mg | 1900.00 mg |
| Citric acid anhydrous EP | 675.00 mg | 839.63 mg |
| Sodium bicarbonate EP | 800.00 mg | 751.00 mg |
| Sodium carbonate anhydrous EP | 410.00 mg | 430.00 mg |
| Sorbitol EP | 275.00 mg | — |
| Orange Flavour, type Firmenich 860.807 TDI | 80.00 mg | — |
| Aspartame EP | 12.00 mg | — |
| Acesulfame potassium EP | 12.00 mg | 4.00 mg |
| Sucralose Tate & Lyle | — | 4.00 mg |
| Macrogol 6000 EP | 24.63 mg | — |
| Strawberry flavour, Type Givaudan PHS-132962 | — | 30.00 mg |
| Tablet weight | 4200.00 mg | 4050.00 mg |

Several bsphosphonates have been identified as pharmaceutical agents that inhibit bone resorption, including:

Alendronate (4-amino-1-hydroxy-butylidene)bis-phosphonate;

Cimadronate [(cycloheptylamino)methylene]bis-phosphonate;

Clodronate (dichloromethyle)-bis-phosphonate;

EB-1053 [1-hydroxy-3-(1-pyrrolidinyl)-propylidene]bis-phosphonate;

Etidronate (1-hydroxyethylidene)-bis-phosphonate;

Ibandronate [1-hydroxy-3-(methylpentylamino)propylidene]bis-phosphonate;

Neridronate (6-amino-1-hydroxyhexylidene)bis-phosphonate;

Olpadronate [3-(dimethylamino)-1-hydroxy-propylidene] bis-phosphonate;

Pamidronate (3-amino-1-hydroxypropylidene)bis-phosphonate;

Risedronate [1-hydroxy-2-3-pyridinyl)-ethylidene]bis-phosphonate;

Tiludronate [[(4-chlorophenyl)thio]methylene]bis-phosphonate

YH 529 [1-hydroxy-2-imidazo-(1,2a)pyridin-3-ylethylidene]bis-phosphonate; and

Zoledronate [1-hydroxy-2-(1H-imidazol-1-yl)ethylidene] bis-phosphonate.

The present invention is directed to an effervescent pharmaceutical formulation comprising, as an active ingredient, a hi sphosphonate. Preferred compounds are selected from the group consisting of: alendronate, cimadronate, clodronate, EB-1053, etidronate, ibandronate, neridronate, olpadronate, pamidronate, risedronate, tiludronate. YH 529, zoledronate, pharmaceutically acceptable salts and esters of the foregoing, and mixtures of the foregoing; the invention is also suitable for the co-administration of other bone metabolism regulators, such as steroid hormones, vitamin D and related compounds, and other orally active agents that are appropriate as adjunctive, co-administered, or synergistic therapeutics in combination with bisphosphonates.

As part of the effervescent system, an acid source selected from the group consisting of: citric acid, tartaric acid, malic acid, fumaric acid, adipic acid, succinic acid; an anhydride of said acids; an acid salt selected. from the group consisting of sodium dihydrogen phosphate, sodium dihydrogen pyrophosphate and sodium acid sulfite and mixtures of the acids, anhydrides and acid salts.

As part of the effervescent system, a carbonate source is selected from the group consisting of: sodium bicarbonate, sodium carbonate, potassium bicarbonate, potassium carbonate, sodium sesquicarbonate, sodiums glycine carbonate, and mixtures thereof.

This invention discloses effervescent formulations that do not use conventional binders, including agents such as polyvinyl pyrrolidone, cellulose derivates, lactose or hypromellose, Sodium chloride, sodium benzoate and sodium sulfate are not used either. Because of the clear degradation product issue related to polyols including sugars, we exclude all sugars (such as mannitol, lactose, dextrose or sorbitol) in any amount from the formulation it is extremely surprising that practical effervescent powders, granules, and especially tablets can be prepared without binders, which also serve to modulate the residual moisturelhumidity in the formula, rendering good material flow and particularly tableting properties.

The invention also discloses elimination of tableting lubricants, which are often selected :from the group consisting of stearic acid salts, powdered sodium benzoate. L-leucine, sodium laurel sulfate, and most notably the polyethylene glycols (PEGs), specifically macrogol 2000-8000; and optionally, one or more additional agents selected from the group consisting of flavoring agents, such as strawberry, apricot, citrus such as orange, cherry, and including colorants and intense sweeteners (including, aspartame or acesulfame K, sucralose, saccharine, cyclamate, thaumatin, steviosides or neohesperidine.

The effervescent pharmaceutical formulation of the present invention may be either a tablet or a powder or granule. To prepare the formulation for ingestion, the tablet or powders are placed in a convenient amount of water, typically 3 to 8 fluid ounces, to produce an effervescent liquid, and the patient drinks the effervescent liquid.

In one embodiment the formulation is a tablet, where the total weight of the tablet ranges from about 1000 mg to about 50,000 mg. In another embodiment, the tablet weight ranges from about 1500 mg to about 20,000 mg and more particularly from about 3,500 mg to about 6,000 mg.

Throughout this specification and claims the term "bisphosphonate" includes the related bisphosphonic acids and salts, and various crystalline and amorphous forms. "Alendronate" includes the related bisphosphonic acid, and salt forms. It includes crystalline, hydrated crystalline, and amorphous forms of alendronate It specifically includes alendronate sodium and alendronate monosodium trihydrate.

Methods for the preparation of bisphosphonates are well known in the art. Methods for the preparation of alendronate and alendronate sodium salt trihydrate are known, in particular U.S. Pat. Nos. 4,922,007, 5,019,651 and 5,510,517, each of which is hereby incorporated by reference.

The amount of active ingredient (API) in the formulation based on alendronate for example, will range from 1 to 280 mg, particularly 10-180 mg and more particularly 40-120 mg of alendronic acid. Exemplary amounts are 10, 35, 45, 50, 70 80, and 100 mg of free alendronic acid. From these amounts one may prepare daily, alternate daily, biweekly, weekly, semiweekly or monthly oral doses. As described above, it is critical to incorporate alendronate or other bisphosphonate into the formula as a finely milled solid or that it be introduced as a very highly dispersed entity. Micronization of the API or spray drying the API onto other formula components are the simplest methods to achieve this result.

In preferred embodiments the effervescent acid is chosen from acid sources which are also sequestering agents. Bisphosphonates, particularly alendronate, can be potent sequestering agents of divalent cations, especially $Ca^{2+}$ and $Mg^{2+}$. If either of these cations is present, alendronate will sequester them, rendering the alendronate less bioavailable. Preferred acid sources that also act as sequestering agents include citric, acid and tartaric acid, and mixtures thereof. The excess citric, acid or tartaric acid binds these divalent ions and inhibits them from complexing with alendromite.

The effervescing carbonate source should be chosen so that it does not contain divalent cations which could be sequestered by the bisphosphonate. Suitable carbonate sources are sodium bicarbonate, sodium carbonate, potassium bicarbonate, potassium carbonate and sodium glycine carbonate. Preferred carbonate sources are sodium bicarbonate, sodium carbonate, and mixtures thereof.

In one aspect of this invention the acid source is present in an amount equal to or greater than the carbonate source, on a molar equivalent basis. Thus, when citric acid is the acid source and sodium bicarbonate is the carbonate source, the mole ratio of citric acid/bicarbonate is at least 1:1 to 1:3, for example. An excess of the organic acid, especially citric acid, is preferred because this acid not only efficiently generates the effervescence, but acts to sequester any ions which might otherwise complex with alendronate, and the excess citrate also acts as a flavor enhancer.

When sodium carbonate is used as the source of carbonate, one equivalent of acid will require a ratio of 2 moles citric acid to 3 moles carbonate, Analogous ratios can be calculated for any source of acid and carbonate, and the carbonate source may be present as a mixture of bicarbonate and carbonate.

For effervescent powder formulations, the composition of the powder is similar to that of the tablet. In preferred formulations the powder is granulated, In one embodiment the effervescing organic acid component contains 20-70% monosodium citrate, preferably 30-60% monosodium citrate or 40-50% monosodium citrate.

A preferred composition contains a buffer system of sodium carbonate, sodium bicarbonate and 20-70% monosodium citrate, resulting in a pH of 4-7 when dissolved in 200 ml of water or a pH of 5-6.

The preferred composition of the invention may have an acid neutralization capacity of 5-20 mEq per tablet or 10-16 mEq per tablet.

In another embodiment the effervescent formulation butlers the pH of a patient's stomach for at least 15 minutes, to 30 minutes, or longer.

The following formulations and manufacturing procedures can be used for manufacture of storage-stable effervescent tablets containing hi sphosphonates, in particular alendronate sodium.

A flow diagram of the manufacturing process is shown in FIG. 1. The present method of manufacture, which does not utilize conventional tableting excipients can only be accomplished with strict adherence to in-process controls. The critical in-process controls include conventional fluidized bed granulation, which requires the use of an aqueous (or organic) binder solution made from e.g. PVP (polyvinylpyrrolidone, a water-soluble polymer), HPMC (hydroxypropyl methylcellulose) or sugar alcohols dissolved in water to be sprayed on. The preferred granulation fluid is pure water.

Surprisingly, a uniform freely flowing smooth granulate results, having reproducible particle size distribution and reproducible compressibility, without any binder or any other lubricant such as PEG; which means there is no trouble with ejection forces (from the dies) or insufficient tablet tensile strength during tableting.

Therefore granules are made without any binder and the final blend doesn't contain any dry binders either, such as mannitol, sorbitol, xylitol, lactose, cellulose etc. Still and quite unexpectedly, we achieve the desired tablet crushing strength of tablet hardnesses in a range of 35 to 120 Newtons, more preferably 50 to 100 Newtons and even more preferably 60 to 90 Newtons. The residual humidity of ready-to-press effervescent mixtures is typically specified to be less than 0.25% to avoid a premature reaction of the product. However, such low humidity levels usually lead to poor compression properties, which are addressed in turn by the addition of dry binders or by granulating with a binder solution. Unexpectedly this theory was found inappropriate for our product. Tablets of sufficient crushing strength can be manufactured at reasonable compression forces, without capping tendency and free of ejection (from the dies) problems.

We experienced no adverse issues with respect to tablet weight variation, thanks to the excellent flowability of the final blend (as a result of the uniform granules) even without using any flow regulator such as fumed silica (Aerosil 200 or similar) This contributes to better stability by avoiding nano-surface induced reactions.

Formula Example Tabulary formulation overview:

|  | Batch | | |
| --- | --- | --- | --- |
|  | Flavour Strawberry | Flavour Apricot | Flavour Free |
| Micronized Sodium alendronate EP | 91.37 mg | 91.37 mg | 91.37 mg |
| Monosodium citrate anhydrous DAC | 1900.00 mg | 1900.00 mg | 1900.00 mg |
| Citric acid anhydrous EP | 839.63 mg | 832.63 mg | 819.63 mg |
| Sodium bicarbonate EP | 751.00 mg | 753.00 mg | 753.00 mg |
| Sodium carbonate anhydrous EP | 430.00 mg | 430.00 mg | 430.00 mg |
| Acesulfame potassium EP | 4.00 mg | 4.00 mg | 3.00 mg |
| Sucralose Tate & Lyle | 4.00 mg | 4.00 mg | 3.00 mg |
| Strawberry flavour, Type Givaudan PHS-132962 | 30.00 mg | — | — |
| Apricot flavour, Type Givaudan 11033-31 | — | 35.00 mg | — |
| Tablet weight | 4050.00 mg | 4050.00 mg | 4000.00 mg |

Manufacturing Process Development

Effervescent tablet formulations require very low residual humidity levels. Therefore a granulation process followed by a drying step was selected as the basic manufacturing principle. Moreover, mono sodium citrate cannot be processed into tablets without. a prior granulation step due to its poor compressibility.

Finally, the following procedure was identified to manufacture a product that meets the specifications: citric acid and mono sodium citrate are pre-blended in fluidized bed equipment and spray granulated with purified water for at least 30 minutes. The resulting granules are dried until the specified loss on drying of <0.15% is achieved (at 75° C., 4 minutes drying duration, 10 g, sample).

After a comminution step the granules are blended with the pre-mix The pre-mix comprises all remaining constituents of the formulation and is manufactured by a series of blending and sieving steps.

The ready-to-press mixture is compressed into tablets of 25 mm diameter and at least 50 N crushing strength on a rotary tablet press, followed by online packaging into strip packs or tubes.

On the way to the final formula and manufacturing principle, the following option were also considered and rejected:

| Parameter investigated | Reason for rejection |
|---|---|
| Direct compression | Loss on drying too high |
|  | Poor compressibility |
|  | Weight and consequential assay variation |
| Addition of macrogol as lubricant | Not necessary; might lead to poorer stability |
|  | Prolongs disintegration time |
| Addition of sorbitol as a filler or dry binder | Can be eliminated but only if appropriate granulation parameters are selected, the achievable crushing strength is sufficient. Risk of instability. |

Batch Formula

The production batch size for the manufacture of the commercial good and the clinical medication is 125,000 tablets. This number represents the final blend batch size that is compressed into effervescent tablets.

TABLE 3

Batch formula

| Component | Composition per unit dose (in mg) | Composition per batch (in kg) | Reference to standards |
|---|---|---|---|
| Micronized Sodium alendronate (+1% technical overage) | 91.37 | 11.421 (+0.114) | Ph. Eur |
| Monosodium citrate anhydrous | 1900.00 | 237.500 | DAC |
| Citric acid anhydrous | 839.63 | 104.953 | Ph. Eur. |
| Sodium hydrogen carbonate (+technical overage*) | 751.00 | 93.875 (+0.376) | Ph. Eur. |
| Sodium carbonate anhydrous | 430.00 | 53.750 | Ph. Eur. |
| Strawberry flavour | 30.00 | 3.750 | Supplier monograph |
| Acesulfame potassium | 4.00 | 0.500 | Ph. Eur. |
| Sucralose | 4.00 | 0.500 | NF |
| Purified water** | Approx. 800.00 | 100.000 | Ph. Eur. |
| Total tablet weight | 4050.00 | 506.249 | |

*A technical overage of 1% is applied to the quantity of sodium hydrogen carbonate blended with sodium alendronate (first step of the preparation of the pre-blend).
**Not present in the final product Description of Manufacturing Process and Process Controls The production batch size is 125,000 tablets. A common granulate comprising all mono sodium citrate and the main part of citric acid is manufactured. Then a pre-mix is manufactured comprising all remaining compounds of the formulation. Finally, the granules and the pre-mix are blended to form the ready-to-press mixture which is compressed into tablets that get strip-sealed in an online process.

Preparation of mono sodium citrate granulate (formulation for 125,000 tablets):

Citric acid and mono sodium citrate are placed into a fluid-bed granulator and spray-granulated with purified water. The granules are then dried until a loss on drying of max, 0.15% is achieved. The granules are then cooled down and the loss on drying re-checked. Finally the granules are passed through a 1.5 mm sieve and stored in closed container with desiccant. The yield is calculated.

Preparation of pre-blend (formulation for 125,000 tablets):

A part of sodium hydrogen carbonate, the sodium carbonate anhydrous and citric acid anhydrous are placed into a container through a 1.5 mm sieve. A part of sodium hydrogen carbonate, the micronized sodium alendronate, :sweeteners and flavour are pre-blended for 15 minutes and passed through. a 0.8 mm oscillating sieve. The remainder of sodium hydrogen carbonate is passed through the sieve. The container is blended for 30 min. Finally the loss on drying is tested. The maximal LOD limit has been established at 0.25%. The yield is calculated.

Preparation of final blend (formulation for 125,000tablets):

The mono sodium citrate granules are placed into a container. The previously prepared pre-blend is then added to the mono sodium citrate granules through a 1.5 mm sieve and blended for 45 minutes. The toss on drying (max. 0.25%) is checked and the yield calculated. The final blend is packed into PE bags with desiccant and then into steel container.

Compressing

The ready-to-press mixture is compressed on a rotary tablet press (Korsch or equivalent) into tablets of 25.0-25.3 mm diameter, 5.4-6.0 mm thickness with an average mass of 4050 mg. During compressing the following IPCs are performed:

Appearance
Dimensions
Average mass
Standard deviation
Hardness
Disintegration time It should be understood that one skilled in this art will recognize equivalent formulations which are intended to be included with the scope of this invention.

Controls f Critical Steps and Intermediates

TABLE 4

| In-Process controls | | |
|---|---|---|
| Test | Limits | Method/Intervals |
| Mono sodium citrate granules | | |
| Loss on drying HR73/75° C./10 g/4 min | Max. 0.15% | Thermo balance/ at the end |
| Yield of final blend | 97.0-100.0% of theoretical yield | At the end |
| Pre-blend | | |
| Loss on drying HR73/75° C./10 g/4 min | Max. 0.25% | Thermo balance/ at the end |
| Yield of final blend | 98.0-101.5% of theoretical yield | At the end |
| Final blend | | |
| Loss on drying HR73/75° C./10 g/4 min | Max. 0.25% | Thermo balance/ at the end |
| Yield of final blend | 97.5-101.0% of theoretical yield | At the end |
| Tablets | | |
| Diameter | 25.0-25.3 mm | Calliper, at beginning |
| Thickness | 5.5-6.1 mm | Calliper, every 20 min. |
| Resistance to crushing | 50-100N | Ph. Eur., current edition, every 20 min |
| Average mass of tablets | 4050 mg | Ph. Eur., current edition, every 20 min. |
| Uniformity of mass | RSD max. 3.0% | Ph. Eur., current edition, every 1 hour |
| Disintegration | Max. 3 min. | Ph. Eur., current edition, at the beginning. |
| Packaging | | |
| Correctness of Lot.-No. | Has to comply | Visual |
| Correctness of expiry date | Has to comply | Visual |

The invention claimed is:

1. A stable effervescent tableted composition, comprising:
    an effective amount of micronized sodium alendronate trihydrate of size distribution about $X_{10}$=2.7 μm, $X_{50}$=6.2 μm, $X_{90}$=13 μm, as a bisphosphonate bone resorption inhibitor,
    an effervescing organic acid component containing citric acid and mono sodium citrate,
    an effervescing base component;
        wherein said tablet has been obtained using a fluidized bed granulation process; has a total weight of 3,500 mg to 6,000 mg, is free from excipients and tableting lubricants which react with said effervescing organic acid component; has a loss on drying of 0.25% (m/m) or less; has a complete disintegration time of no more than 180 seconds when placed in 3 to 8 fluid ounces of water at between 5-20° C.; and said alendronate is completely solubilised in water within 2 minutes without stirring.

2. The composition of claim 1, which has a tablet hardness of 35 to 120 Newtons.

3. The composition of claim 2, having tablet hardnesses in the range of 60 to 90 Newtons.

4. The composition of claim 1, having a disintegration time between 60 and 130 seconds.

5. The composition of claim 1, wherein the effervescing organic acid component contains 20-70% monosodium citrate.

6. The composition of claim 1, wherein the effervescing organic acid component contains 30-60% monosodium citrate.

7. The composition of claim 1, wherein the effervescing organic acid component contains 40-50% monosodium citrate.

8. The composition of claim 1, wherein said effervescing organic acid component and effervescing, base component provide a buffer system of sodium carbonate, sodium bicarbonate and 20-70% monosodium citrate, resulting in a pH of 4-7 when dissolved in 200 ml of water.

9. The composition of claim 8, wherein the buffer system results in a pH of 5-6 when dissolved in 200 ml of water.

10. The composition of claim 8, having an acid neutralization capacity of 5-20 mEq per tablet.

11. The composition of claim 8, having an acid neutralization capacity of 10-16 mEq per tablet.

12. The composition of claim 8, which buffers the pH of a patient's stomach for at least 15 minutes.

13. The composition of claim 1, comprising a daily, weekly, bi-weekly, or monthly oral dose of alendronate.

14. The composition of claim 1, further comprising a flavouring component selected from the group consisting, of strawberry, apricot, citrus, and cherry, optionally containing sweeteners selected from the group consisting of aspartame, acesulfame K, sucralose, saccharine, cyclamate, thaumatin, steviosides and neohesperidine.

15. The composition of claim 1, further comprising a steroid hormone, vitamin D, or an adjunctive therapeutic given in combination with alendronate.

* * * * *